United States Patent
Massey et al.

(10) Patent No.: US 7,365,651 B2
(45) Date of Patent: Apr. 29, 2008

(54) METHOD AND APPARATUS FOR SELECTING A USER INTERFACE

(75) Inventors: Noel Massey, Carpentersville, IL (US);
Robert Gardner, Gilbert, AZ (US);
Bradford Miller, Austin, TX (US)

(73) Assignee: Motorola, Inc., Schaumburg, IL (US)

( * ) Notice: Subject to any disclaimer, the term of this patent is extended or adjusted under 35 U.S.C. 154(b) by 1151 days.

(21) Appl. No.: 10/223,979

(22) Filed: Aug. 20, 2002

(65) Prior Publication Data

US 2004/0037236 A1 Feb. 26, 2004

(51) Int. Cl.
*G08G 1/09* (2006.01)
(52) U.S. Cl. .................... 340/905; 340/990; 701/1
(58) Field of Classification Search ........... 340/905, 340/990, 995.1, 432, 575; 701/1, 29
See application file for complete search history.

(56) References Cited

U.S. PATENT DOCUMENTS

| | | | |
|---|---|---|---|
| 4,219,800 A | 8/1980 | LeViness | |
| 5,432,509 A | 7/1995 | Kajiwara | |
| 6,061,610 A | 5/2000 | Boer | |
| 6,262,657 B1 * | 7/2001 | Okuda et al. | 340/439 |
| 6,285,279 B1 | 9/2001 | Yamazaki | |
| 6,356,812 B1 * | 3/2002 | Cragun | 701/1 |
| 6,791,472 B1 * | 9/2004 | Hoffberg | 340/905 |
| 6,975,932 B2 * | 12/2005 | Obradovich | 701/96 |
| 6,982,635 B2 * | 1/2006 | Obradovich | 340/439 |
| 2002/0120374 A1 * | 8/2002 | Douros et al. | 701/29 |

* cited by examiner

*Primary Examiner*—Phung T. Nguyen

(57) ABSTRACT

A controller (10) senses via one or more sensors (12) parameters that correspond to likely cognitive loading for the driver of a vehicle. Based upon a sense of this cognitive loading, the controller (10) selects a particular user interface mode from amongst a plurality of user interface modes when receiving a message via a wireless unit (11) intended for the driver of the vehicle. In general, the selected user interface will present a corresponding cognitive challenge that is reasonable in view of the present cognitive load being experienced by the driver. In one embodiment, the sensor information can be used to also estimate the likely duration of present cognitive loading. This window-of-opportunity information is then additionally used to select a particular user interface option.

33 Claims, 2 Drawing Sheets

METHOD AND APPARATUS FOR SELECTING A USER INTERFACE

TECHNICAL FIELD

This invention relates generally to user interfaces and more particularly to user interfaces as used with communications devices.

BACKGROUND

User interfaces for various communications devices are well known in the art. In general, such user interfaces often include one or both of a presentation feature (such as, for example, an annunciation feature to alert a user that a communication has arrived or is being initiated) and an interaction capability (to permit, for example, a user to accept an incoming call or to respond to a data message such as an email or a two-way page). Generally speaking, while some communications platforms provide for a variety of selectable presentation and/or interaction user interface selections, the platform will use a given selection as chosen by the user until the user themselves changes the selection. For example, a device may offer three different annunciation tones. A user can select any of the three tones, and once selected, the device will use that selected tone unless and until the user selects a different tone.

It is also known that many users of such devices will experience varying levels of cognitive loading during the course of a day (that is, the degree to which the user must focus and/or concentrate on a given task or activity will change over time). One particular area of interest in this regard concerns drivers of terrestrial vehicles (such as automobiles, trucks, buses, and the like). Cognitive loading for a driver of such a vehicle can and will vary as a function of a wide-ranging set of variables, including but not limited to roadway conditions, weather conditions, proximal traffic, time of day and/or the day of the week, and social conditions then being experienced by the driver, to name but a few.

To date, the relatively static user interface offered by prior art communications devices may, or may not, be appropriately user-friendly for a given user as a function, in part, of the cognitive loading that the given user is experiencing at any particular time. When the user interface is inappropriate for a given moment, the user's sense of satisfaction with the device and/or their ability to simply effect a successful interaction with the device can be somewhat or even significantly impaired.

BRIEF DESCRIPTION OF THE DRAWINGS

The above needs are at least partially met through provision of the method and apparatus for selecting a user interface described in the following detailed description, particularly when studied in conjunction with the drawings, wherein.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are typically not depicted in order to facilitate a less obstructed view of these various embodiments of the present invention.

DETAILED DESCRIPTION

Generally speaking, pursuant to these various embodiments, one or more parameters that correspond, at least in part, to cognitive loading as is likely experienced by the driver of a terrestrial vehicle are monitored. Based upon such monitoring, one or more user interface options for a communications device are selected for use at a given time.

In one embodiment, the user interface options can include either or both presentation and interaction modes. For example, the presentation modes can include a plurality of presentation modes and the interaction modes can include a plurality of interaction modes. The particular presentation and/or interaction mode can be selected, as desired, based upon a sense of the present and/or near term cognitive loading being experienced by the vehicle driver. For example, in one embodiment, a particular user interface mode can be selected as a function of both the present cognitive loading for the driver and an estimate for the likely continued duration of that level of cognitive loading.

Figure 1:
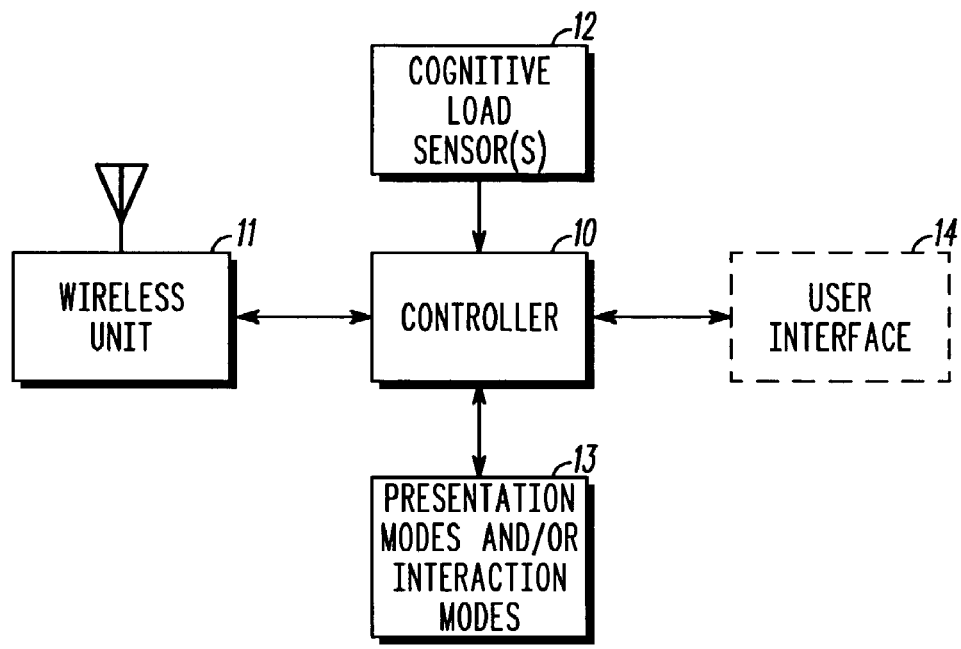
FIG. 1 comprises a block diagram of an apparatus as configured in accordance with an embodiment of the invention.

Referring now to the drawings, and in particular to FIG. 1, a generalized platform for supporting a variety of embodiments will be described. In general, a controller 10 couples to a wireless unit 11 and one or more cognitive load sensors 12. In addition, the controller 10 has access to a plurality 13 of presentation modes and/or interaction modes, which modes are used to control at least aspects of an optional user interface 14. The controller 10 can be realized through various mechanisms including both programmable and hard-wired configurations. In a preferred embodiment, the controller 10 will comprise an at least partially programmable platform such as a microprocessor or, in an appropriate application, a microcontroller, digital signal processor, programmable gate array, or the like.

The wireless unit 11 can be any one-way or two-way wireless communication device, including various generations and formats of wireless voice and/or data telephony and dispatch platforms. For many applications, the benefits of these embodiments may be more readily realizable when the wireless unit 11 comprises a simplex or half-duplex device (such as a one-way or two-way selective call device or a wireless email platform, for example).

In a preferred embodiment, the controller 10 and wireless unit 11 are both situated in a terrestrial vehicle. Significant flexibility exists, however, regarding whether these two components share, for example, a common housing. If desired, these components can be physically separated and couple via a wired or wireless link in accordance with well understood prior art technique.

As already noted, the controller 10 also couples to one or more cognitive load sensors 12. These sensors 12 serve to monitor one or more parameters that correspond, at least indirectly, to cognitive loading as may be experienced by a driver of the vehicle. (Sensors that hold the potential for directly measuring such cognitive loading are likely, at present, to be relatively inconvenient at best for use during ordinary driving. At such time as such sensors may become more practical and available, however, they could be readily used here for the purposes described.) The sensors 12 can be either mounted in the vehicle itself or external thereto (when external sensors are used, a wireless link, for example, can be used to communicate information from the sensor to the controller 10).

Various sensors can be utilized effectively in this role. For example, in general, sensors that provide information regarding the conditions of the roadway upon which the vehicle is traveling can provide information that relates to cognitive loading for the driver. Roadway condition information can include (without limitation) items such as:

Present or upcoming curves;
Alterations to minimum or maximum speed limits;
An increasing or decreasing number of lanes;
Proximity of controlled and uncontrolled intersections;
Traffic control signal status (such as red lights, green lights, and so forth);
Proximity of emergency vehicles (such as fire engines and ambulances);
Urban versus rural roadside conditions;
Roadway signs (such as stop signs, yield signs, and so forth);
Proximity of road construction crews and/or projects; and
Road surface conditions (such as slick, bumpy, and so forth).

Information regarding such environmental facets can be obtained in various ways. One particularly promising approach would be to employ a digital short range communications (DSRC) receiver that can compatibly receive DSRC broadcasts from various vehicular and roadway beacons. The Federal Communications Commission in the United States has presently at least tentatively identified spectrum that can be used for such journey-related information. The American Society for Testing and Materials presently acts as a standards development group to define such a DSRC service to support provision of journey-related information to vehicular users. At present, the over-the-air interface has not been defined (though at least two wireless local area network systems—the I.E.E.E.#802.11A and Motorola's control channel based Freespace system—have been proposed and are being considered). This group has, however, made considerable progress towards defining the features that the service will support. In particular, such a journey-related information provision system should ultimately provide roadside information and corresponding vehicle-to-vehicle communications to support both public safety and private requirements (depending upon the application transmission range will likely vary from fifteen meters to three hundred meters).

Such a system could readily source any or all of the information presented above, and this information could be correlated to a level of cognitive loading for a driver (for example, cognitive loading can be viewed as likely being higher during heavy traffic with poor visibility with quickly varying road surface conditions and relatively lower during light traffic or while stopped at a lengthy stop light). Other systems, such as in-vehicle radar or ultrasonic transducers could also be used to attain at least some of the above information, as could imaging systems that make use of pattern matching programs to detect, for example, construction barriers, lane alterations, shoulder conditions, vehicle proximity, and so forth.

One could also employ sensors that detect vehicle parameters that can reasonably relate to cognitive loading. For example, detectors could be used to monitor vehicle suspension activity, steering manipulations, speed and/or acceleration, headlight usage, frequency and/or intensity of braking, and so forth. Again, in general, such information can be used to assess cognitive loading by correlating the monitored parameter to a likely increased or decreased need for attention and/or focus on the part of the driver.

One could also employ sensors to monitor the driver and/or the cockpit environment for signs that may relate to cognitive loading. For example, passenger sensors could be used to detect the presence of passengers (the presence of passengers, for many individuals, may tend to increase their relative cognitive loading due to the need to effect appropriate social behaviors and interaction). Eye position detectors and so-called glance detectors could be used to ascertain, at least to some degree, the extent to which the driver appears to be attempting to remain informed and alert with respect to a variety of internal or external stimuli. Sound detectors, speech recognition platforms, and voice-stress detectors could be used to assess a potential (or actual) level of social activity and/or intensity within the cockpit, which again can reasonably correlate to anticipated cognitive loading for the driver. Nod detectors could also potentially be used as head nodding by a vehicle driver may also provide some indication of the driver's cognitive condition.

These and other sensors can all be used as desired and/or as appropriate to a given application to monitor parameters that correspond to likely cognitive loading as experienced by the driver of a terrestrial vehicle. The sensors mentioned are generally understood in the art and hence further elaboration will not be presented here for the sake of brevity and the preservation of focus.

The data obtained from such sensors could be represented in a variety of ways. For example, in one embodiment, cognitive loading could be represented as either "high" or "low." Thresholds are then set for each category of sensor data that correspond to such loading ratings. For example, when using a glance detector sensor, a given rate R of glancing can be used as the threshold to differentiate between high and low cognitive loading. So configured, a rate of glancing that is less than the given rate R would be interpreted as a low level of cognitive loading and a rate of glancing that is greater than the given rate R would be interpreted as a high level of cognitive loading. (It should be understood that this particular example is intended to be illustrative of the concept. For some purposes or in some cases, the opposite may hold true. That is, a very low rate of glancing may be an indication of a relatively high cognitive load.) Similarly, a greater number of levels of cognitive loading could be defined, such as "high," "medium," and "low." Again, corresponding thresholds for the particular monitored parameters would be selected to correspond as desired to the selected levels of cognitive loading.

Information indicative of cognitive loading as received from multiple differing sensors could be combined and integrated as desired. For example, such sensor inputs could be normalized with respect to one another to permit summation and averaging of the sensor inputs. Again, predetermined thresholds for the averaged sensor inputs could then be correlated to particular cognitive loading levels. Where a particular sensor contributes information considered to be a more reliable indication of cognitive loading, that sensor information could also be weighted accordingly to ensure that such sensor input exerted a greater influence with respect to assessing cognitive loading.

Figure 2:
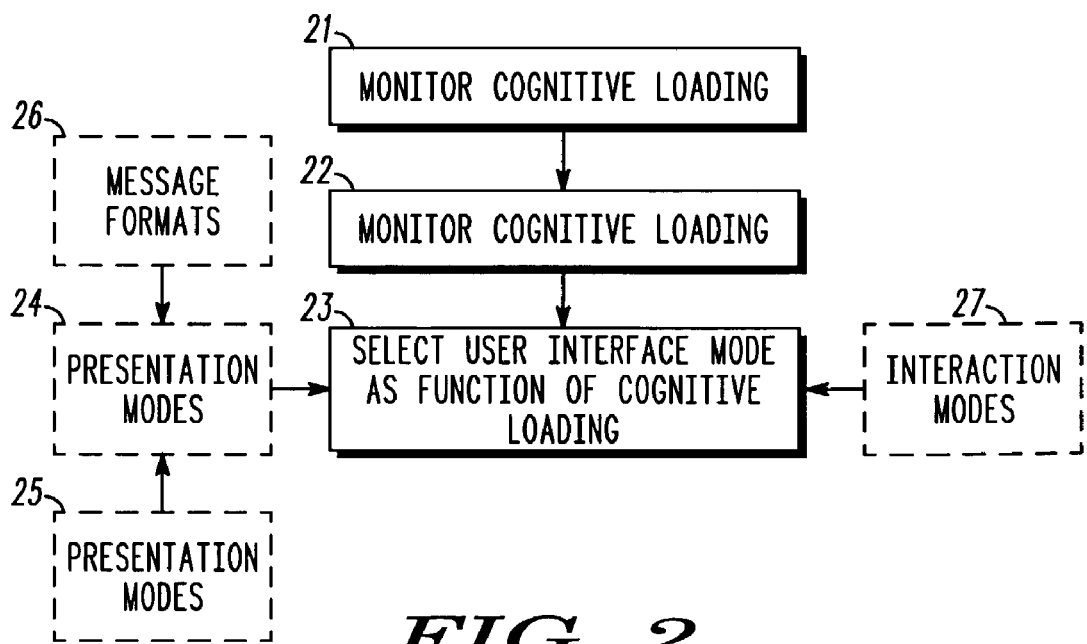
FIG. 2 comprises a general flow diagram as configured in accordance with an embodiment of the invention, FIG. 3 comprises a flow diagram as configured in accordance with an alternative embodiment of the invention.

So configured, the controller 10 receives information from the sensors 12 and processes that information to develop an assessment of the cognitive loading that is likely to be experienced by a driver of the corresponding vehicle. The controller 10 uses this information regarding cognitive loading to then select a particular user interface mode. For example, and referring now to FIG. 2, the controller 10 monitors 21 cognitive loading as already described. When a wireless communication is received 22 via the wireless unit 11, the controller then selects 23 a particular user interface mode as a function of the cognitive loading information. Selecting a particular user interface mode can include selection of either or both of a presentation mode 24 and an interaction mode 27.

At one extreme and in one embodiment, when the cognitive loading is high, one presentation mode the controller 23 can select is the option to not present the incoming message to the vehicle driver. Such an action would presumably reflect the belief that the driver is simply too preoccupied with other events and circumstances to permit useful receipt of the present incoming message. In a preferred embodiment, when not presenting such an incoming message, the controller 10 could automatically transmit a message to the originating party to acknowledge receipt of the message and to advise the originating party that the message has nevertheless not been delivered. In addition, or in the alternative, the controller 10 could also automatically reroute the message to another destination. For example, upon determining that the driver's present cognitive loading is relatively high, the controller 10 could forward the message to the driver's email account at the driver's home or place of employment for later viewing by the driver.

The various presentation modes 24 available to the controller 10 could include, in a preferred embodiment, either or both of annunciation modes 25 and message formats 26. Annunciation modes 25 refer to the means by which the controller 10 can alert the driver to the existence of an incoming message. For example, in a preferred embodiment, a plurality of annunciation modes 25 could be provided, including various audible and visual annunciation modes. A first annunciation mode could be relatively insistent and demanding and could be appropriate for use during periods of low cognitive loading. Another annunciation mode could be relatively timid and tentative in tone or appearance, thereby tending to more intuitively give the driver the apparent option to ignore the annunciation and, in effect, the message. The latter annunciation mode would be more appropriate for use during periods of higher cognitive loading.

In a similar fashion, different message formats 26 could be made available for use in this same way. For example, a plurality of message presentation formats could be provided, including full text formats and abridged text formats for data messages. An abridged text format could be realized in various ways. For example, a message could simply be truncated to yield a message of reduced length. As another example, certain portions of a message (such as certain header content) could be deleted from presentation. As yet another example, the substantive content of a message could be abridged through substantive summation thereof. Such a substantive summation could be provided in the first instance by the party originating the message or could be automatically generated by a semantic analysis and text generation program as is known and understood in the art. As yet another example, the speed at which a message is presented (either as scrolling text, audibilized text, or as recorded audio (such as voicemail)) can be slowed down (to accommodate higher cognitive loading periods) or sped up (to accommodate low periods of cognitive loading). So configured, full text message presentations could be used during periods of lower cognitive loading and abridged message presentations could be used during periods of higher cognitive loading.

In some cases, it may be possible to ascertain not only the current likely cognitive load for a driver but also the likely duration of that level of loading. When such information is available, the ability to manipulate the presentation of the message with respect to length and/or brevity can be specifically dynamically tailored to attempt to assure that the entire message (regardless of whether complete or abridged) can likely be fully delivered within the window of opportunity as so determined. Furthermore, the anticipated response time of the driver to the message may be taken into account so that both the message delivery and driver's response are reasonably likely to be completed within the window of opportunity.

In a preferred embodiment, the plurality of message formats 26 would also include formats that use different presentation media. For example, a visual display of a text message could comprise one presentation media and a text-to-speech synthesis platform as known in the art could comprise another presentation media. Another example would be to present a graphic image, such as a relevant icon, that reasonably corresponds to the message content, source, or other aspect or property of interest. The visual display could be selected during periods of lower cognitive loading and the audio alternative could be used during periods of higher cognitive loading.

It should also be understood that differing presentation media could be combined in different ways with other differing message formats to provide even more options for the controller 10 to select from.

As noted earlier, the controller 10, when selecting 23 a particular user interface mode, can also, in an appropriate embodiment, select a given interaction mode 27. The interaction modes 27 refer to the opportunities provided to the driver to respond to the message as presented to the driver. Such modes can include all interaction opportunities, including but not limited to storing, deleting, replying, and forwarding (with or without additional commentary as to all of these options). For example, in a preferred embodiment, the interaction modes 27 could include one or more interaction modes having a primary interaction mode that comprises only a limited set of predetermined candidate responses from which the driver can select when replying to a given message. Such interaction modes would potentially be suitable for use during periods of higher cognitive loading. In a preferred embodiment, such interaction modes could also offer a driver a selectable secondary interaction mode that would permit, for example, a free text response by the driver. Although such a free text opportunity may be inconsistent with the appearance of high cognitive loading, for whatever reason the driver may wish to override the reply opportunity as automatically selected by the controller 10. Similarly, the interaction modes 27 could include one or more interaction modes having a primary interaction mode comprising a free text entry mechanism for use by the driver when replying to the message. Such a free test entry mechanism would ordinarily be appropriate for selection and use during periods of low cognitive loading. Nevertheless, it would also be possible here to again offer the driver an option to select a menu of previously formed candidate responses from which the driver can select.

Figure 3:
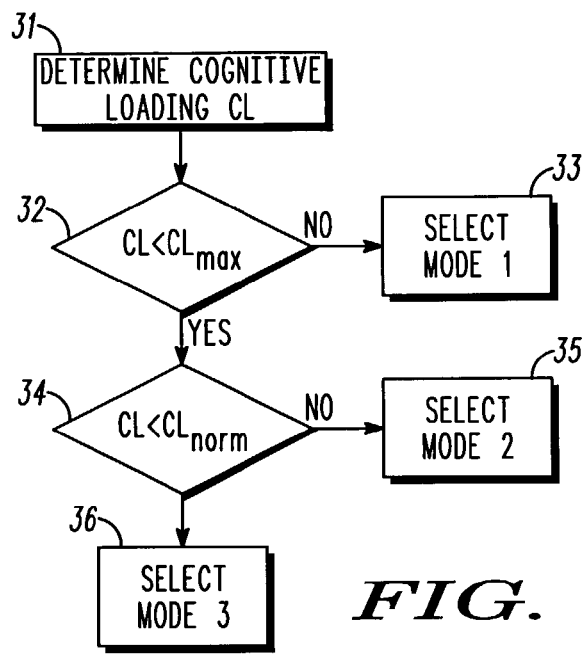

It can therefore be seen that a given user interface mode as selected by the controller 10 can comprise a particular presentation mode as selected from amongst a plurality of presentation modes, a particular interaction mode as selected from amongst a plurality of interaction modes, or a combination of both. As one illustrative embodiment, three levels or zones of cognitive loading can be predefined and specific sensor levels as correspond to the boundaries or thresholds that separate those levels or zones can be similarly defined. The user interface mode selection 23 activity could therefore be represented as shown in FIG. 3. A present level CL of cognitive loading is determined 31 and then compared 32 against a first threshold value $CL_{max}$ that, in this example, represents a maximum level of cognitive loading. When the present cognitive load CL is greater than the maximum threshold level $CL_{max}$, a first user interface mode is selected 33. This first user interface mode would likely be an interface mode comprised of presentation and/or interaction modes that tend to minimize unduly adding to the already high cognitive loading on the vehicle driver. When this comparison indicates instead that the present level of cognitive loading CL is less than the maximum threshold level $CL_{max}$, the controller 10 determines 34 whether the present level of cognitive loading CL is less than a normal level of cognitive loading $CL_{norm}$. When not true, therefore indicating that the cognitive load is within a normal range of expected loading, a second user interface mode is selected 35. This second user interface mode would likely be an interface mode comprised of presentation and/or interaction modes that tend to complement a normal level of cognitive loading on the vehicle driver. When this comparison is true (therefore indicating that the present cognitive loading is relatively low), a third user interface mode is selected 36. This third user interface mode would likely be an interface mode comprised of presentation and/or interaction modes that can more freely present cognitive challenge to the driver.

As noted earlier, the controller 10 can utilize sensor input to ascertain a likely level of cognitive loading for a vehicle driver at a given point in time. In some instances, the sensor data may facilitate an ability to predict the likely duration for that ascertained level of cognitive loading to continue. In addition, the data may support a reasonable prediction regarding the way in which cognitive loading is likely to change at the end of that estimated duration. For example, when the sensor data includes information that the vehicle is presently stopped at a traffic light, and when the sensor data further includes information regarding the point in time when that traffic light will change to green (as may be provided in certain DSRC implementations), the controller 10 can reasonably estimate the duration of the present level of cognitive loading (as that level will likely change when the traffic light changes and the point in time when that will occur is now known to the controller 10). This information can then be additionally used to make appropriate selections from amongst a plurality of user interface modes.

Figure 4:
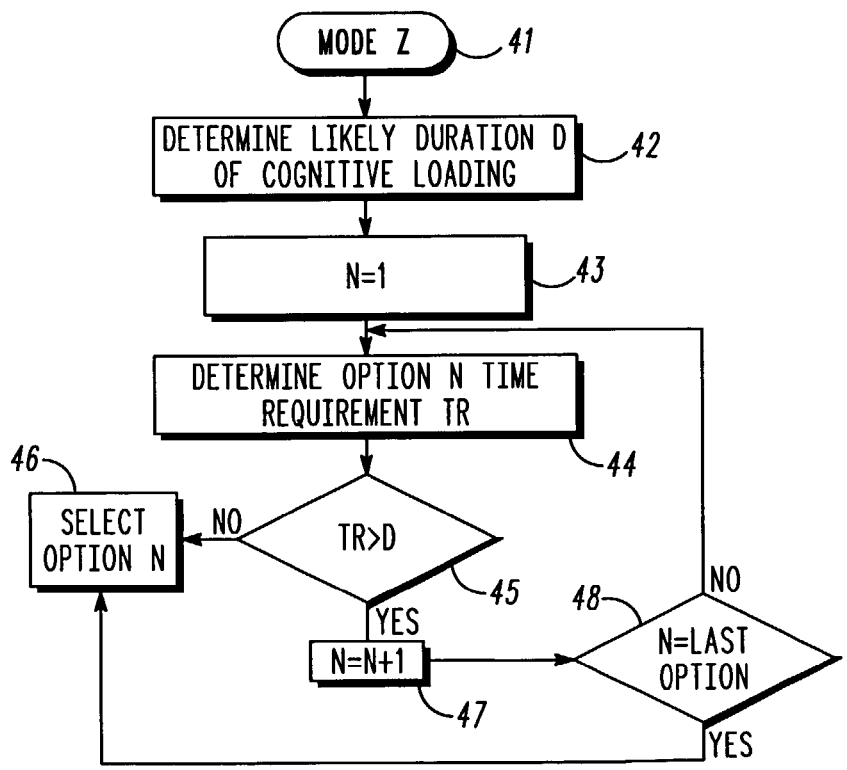
FIG. 4 comprises a detail flow diagram as configured in accordance with an alternative embodiment of the invention.

For example, and referring now to FIG. 4, based upon previous processing as described above, the controller can have ascertained a certain current level of cognitive loading and can therefore have selected a particular mode 41 (in this example, mode Z). The controller 10 can then determine 42 the likely duration D for that level of cognitive loading. A variable N is then assigned 43 to be "1" and the controller 10 determines 44 the time requirement TR that will likely be required when using user interface option N. The controller 10 then compares 45 that time requirement TR for option N with the likely present duration D to ascertain whether sufficient time exists to make selection of this particular option a reasonable selection. When sufficient time is available, then that particular option N is selected 46 and used as described above. When sufficient time does not likely exist, the controller 10 can increment 47 the N count and ascertain 48 whether the next option represents the last option available. When true, that last option is selected. Otherwise, the above comparison process repeats to continuing seeking an option that can likely be implemented within the available opportunity horizon.

In the embodiment just described, the substantive content of the message itself does not play a significant part in selecting a particular option. In fact, if desired and as appropriate to a given application, the substantive content can be used as yet another parameter of interest when selecting a particular option. For example, when the content can be identified as especially important (for example, by reference to an accompanying flag or indicator of importance and/or by an automatic review of the message content for keywords, semantics, or the like as well understood in the art), a particular option may be selected for that message notwithstanding the fact such a selection may otherwise represent a higher incremental cognitive load increase than might otherwise be desired or accepted.

So configured, these various embodiments offer a wide degree of flexibility and options to accommodate a wide variety of message types, communication devices, driver circumstances, and even individual driver characteristics by facilitating selection and use of a communication device user interface that meshes better with a driver's given cognitive circumstances than a static user interface. As a result, it can be expected that the driver's user experiences will tend to be more successful over time.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method comprising:
receiving a wireless communication for a terrestrial vehicle driver, which wireless communication does not relate to the navigation and operation of the terrestrial vehicle and which comprises a message having substantive content;
monitoring at least one parameter that corresponds to cognitive loading as is likely experienced by the vehicle driver;
selecting at least one of:
a communication presentation mode that corresponds to presentation of the substantive content that relates to the wireless communication from amongst a plurality of communication presentation modes that each provide for a different way of presenting the substantive content; and
a communication interaction mode that corresponds to facilitating a response by the terrestrial vehicle driver to the wireless communication from amongst a plurality of communication interaction modes;
as a function, at least in part, of the at least one parameter.

2. The method of claim 1 wherein receiving wireless communication comprises receiving one of a simplex and a half-duplex wireless communication.

3. The method of claim 2 wherein comprises receiving one of a simplex and a half-duplex wireless communication includes receiving a data message.

4. The method of claim 1 wherein monitoring at least one parameter that corresponds to cognitive loading as is likely experienced by the vehicle driver includes receiving wireless messages regarding roadway conditions that are likely to be encountered by the vehicle driver.

5. The method of claim 1 wherein monitoring at least one parameter that corresponds to cognitive loading as is likely experienced by the vehicle driver includes receiving wireless messages regarding weather conditions that are likely to be encountered by the vehicle driver.

6. The method of claim 1 wherein monitoring at least one parameter that corresponds to cognitive loading as is likely experienced by the vehicle driver includes receiving wireless messages regarding traffic control devices that are likely to be encountered by the vehicle driver.

7. The method of claim 6 wherein the traffic control devices include at least one of a stop sign, a traffic control light, and a barrier.

8. The method of claim 1 wherein monitoring at least one parameter that corresponds to cognitive loading as is likely experienced by the vehicle driver includes monitoring at least one in-vehicle sensor.

9. The method of claim 8 wherein the at least one in-vehicle sensor comprises at least one of a suspension monitor, a steering monitor, a radar, an eye position and glance detector, a nod detector, an ultrasonic transducer, a passenger sensor, a voice-stress detector, a voice recognition platform, and a sound detector.

10. The method of claim 1 wherein monitoring at least one parameter that corresponds to cognitive loading as is likely experienced by the vehicle driver includes monitoring at least one of a time of day and a day of the week.

11. The method of claim 1 wherein selecting at least one of a communication presentation mode from amongst a plurality of communication presentation modes includes selecting an annunciation mode from amongst a plurality of annunciation modes.

12. The method of claim 11 wherein selecting an annunciation mode from amongst a plurality of annunciation modes includes selecting from amongst a plurality of audible annunciation modes.

13. The method of claim 11 wherein selecting an annunciation mode from amongst a plurality of annunciation modes includes selecting from amongst a plurality of visual annunciation modes.

14. The method of claim 1 wherein selecting at least one of a communication presentation mode from amongst a plurality of communication presentation modes includes selecting a particular message presentation format from amongst a plurality of message presentation formats.

15. The method of claim 14 wherein selecting a particular message presentation format includes selecting a message presentation format that abridges the wireless communication.

16. The method of claim 14 wherein selecting a particular message presentation format includes selecting from amongst a plurality of message presentation formats wherein at least some of the message presentation formats comprise presentation formats that use, at least in part, differing presentation media from one another.

17. The method of claim 1 wherein selecting at least one of a communication presentation mode from amongst a plurality of communication presentation modes includes selecting from amongst a plurality of message presentation formats that include not presenting a given message to the vehicle driver.

18. The method of claim 17 wherein not presenting a given message to the vehicle driver includes automatically transmitting a message to an originating party of the given message.

19. The method of claim 17 wherein not presenting a given message to the vehicle driver includes automatically rerouting at least a portion of the given message to an alternative destination.

20. The method of claim 1 wherein selecting a communication interaction mode from amongst a plurality of communication interaction modes includes selecting from amongst a plurality of communication interactions modes that include at least one of:
a primary communication interaction mode comprising only a limited set of predetermined candidate responses from which the vehicle driver can select; and
a primary communication interaction mode comprising at least a free text response tool such that the vehicle driver can enter a free text response.

21. The method of claim 20 wherein the primary communication interaction mode comprising only a limited set of predetermined candidate responses from which the vehicle driver can select includes a secondary communication interaction mode comprising at least a free text response tool such that the vehicle driver can enter a free text response.

22. The method of claim 20 wherein the primary communication interaction mode comprising at least a free text response tool such that the vehicle driver can enter a free text response includes a secondary communication interaction mode comprising a limited set of predetermined candidate responses from which the vehicle driver can select.

23. The method of claim 1 wherein selecting at least one of a communication presentation mode and a communication interaction mode as a function, at least in part, of the at least one parameter includes selecting at least one of a communication presentation mode and a communication interaction mode as a function, at least in part, of an anticipated duration of a particular level of cognitive loading as is likely to be experienced by the vehicle driver.

24. The method of claim 1 wherein selecting at least one of a communication presentation mode and a communication interaction mode as a function, at least in part, of the at least one parameter includes selecting at least one of a communication presentation mode and a communication interaction mode as a function, at least in part, of an anticipated level of cognitive loading as is likely to be experienced by the vehicle driver.

25. The method of claim 1 wherein selecting at least one of a communication presentation mode and a communication interaction mode as a function, at least in part, of the at least one parameter includes selecting at least one of a communication presentation mode and a communication interaction mode as a function, at least in part, of an anticipated change of cognitive loading as is likely to be experienced by the vehicle driver.

26. An apparatus comprising:
a cognitive load sensor having at least one input to receive information that corresponds to cognitive loading likely to be experienced by a vehicle driver;
a wireless communications device having at least one of a plurality of selectable communication presentation modes that each provide for a different way of presenting a given item of substantive content and a plurality of selectable communication interaction modes and having an input to receive a wireless communication comprising, at least in part, the given item of substantive content, wherein the given item of substantive content does not relate to navigating or operating a vehicle being driven by the vehicle driver; and a communications device controller that is operably coupled to the cognitive load sensor and the wireless communications device such that the communications device controller provides control signals to the wireless communications device to select at least one of the selectable communication presentation modes and the selectable communication interaction modes as a function of the cognitive loading likely to be experienced by the vehicle driver to thereby select a particular way of presenting the given item of substantive content to the vehicle driver.

27. The apparatus of claim 26 wherein the wireless communications device comprises one of a simplex and a half-duplex wireless communications device.

28. The apparatus of claim 26 wherein the information that corresponds to cognitive loading reflects, at least in part, at least one of roadway conditions that are likely to be encountered by the vehicle driver, weather conditions that are likely to be encountered by the vehicle driver, and traffic control devices that are likely to be encountered by the vehicle driver.

29. The apparatus of claim 26 wherein the information that corresponds to cognitive loading reflects, at least in part, information from at least one in-vehicle sensor.

30. The apparatus of claim 29 wherein the at least one in-vehicle sensor comprises at least one of a suspension monitor, a steering monitor, a radar, an ultrasonic transducer, a passenger sensor, a voice-stress detector, a voice recognition detector, and a sound detector.

31. The apparatus of claim 26 wherein the plurality of selectable communication presentation modes include a plurality of annunciation modes.

32. The apparatus of claim 26 wherein the plurality of selectable communication presentation modes include a plurality of message presentation formats.

33. The apparatus of claim 26 wherein the communications device controller includes means for at least estimating when a significant alteration in cognitive loading as may be experienced by the vehicle driver will occur.

* * * * *